United States Patent
Kalinichev et al.

(10) Patent No.: US 11,975,055 B2
(45) Date of Patent: May 7, 2024

(54) SUPPRESSION OF BONE CANCER-INDUCED ALLODYNIA

(71) Applicant: IPSEN BIOPHARM LIMITED, Wrexham (GB)

(72) Inventors: Mikhail Kalinichev, Wrexham (GB); Christine Favre, Wrexham (GB)

(73) Assignee: IPSEN BIOPHARM LIMITED, Wrexham (GB)

(*) Notice: Subject to any disclaimer, the term of this patent is extended or adjusted under 35 U.S.C. 154(b) by 758 days.

(21) Appl. No.: 17/056,527

(22) PCT Filed: May 21, 2019

(86) PCT No.: PCT/EP2019/063069
§ 371 (c)(1),
(2) Date: Nov. 18, 2020

(87) PCT Pub. No.: WO2019/224184
PCT Pub. Date: Nov. 28, 2019

(65) Prior Publication Data
US 2021/0205422 A1    Jul. 8, 2021

(30) Foreign Application Priority Data
May 21, 2018 (EP) .................... 18173441

(51) Int. Cl.
*A61K 38/48* (2006.01)
*A61P 25/02* (2006.01)
*A61P 29/00* (2006.01)

(52) U.S. Cl.
CPC .......... *A61K 38/4893* (2013.01); *A61P 29/00* (2018.01); *A61K 38/482* (2013.01); *A61K 38/4886* (2013.01); *A61P 25/02* (2018.01); *C12Y 304/24069* (2013.01)

(58) Field of Classification Search
None
See application file for complete search history.

(56) References Cited

U.S. PATENT DOCUMENTS

| | | |
|---|---|---|
| 6,641,820 B1 | 11/2003 | Donovan |
| 2004/0131615 A1* | 7/2004 | Shelton ................. C07K 16/22 530/388.25 |
| 2011/0206752 A1 | 8/2011 | Serraima et al. |
| 2012/0230975 A1 | 9/2012 | Foster et al. |
| 2014/0099294 A1 | 4/2014 | Dolly et al. |

FOREIGN PATENT DOCUMENTS

RU   2515054 C2   5/2014

OTHER PUBLICATIONS

Clohisy et al. Bone Cancer Pain. Clin Orthop Relat Res (2003), 415 Suppl:S279-88. (Year: 2003).*
Vacca et al. Botulinum toxin A increases analgesic effects of morphine, counters development of morphine tolerance and modulates glia activation and I opioid receptor expression in neuropathic mice. Brain, Behavior, and Immunity (2013), 32, 40-50. ( Year: 2013).*
Clohisy et al. Bone Cancer Pain. Cancer 2003;97(3 Suppl): 866-73. (Year: 2003).*
Intiso et al., Toxins, 7:2454-2480 (2015).
Falk et al., European Journal of Pain, 19:305-312 (2015).
Zhu et al., Drug Design, Development and Therapy, 9:4239-4245 (2015).
International Search Report dated Jul. 18, 2019, in PCT/EP2019/063069.
V.G. Belikov, Pharmaceutical Chemistry, Moscow, Vysshaya Shkola, 1993, pp. 27-29.
"Amino acids, peptides and proteins", H.-D. Jacubke et al., Moscow: Mir, 1985, pp. 92-94.

* cited by examiner

*Primary Examiner* — Sean C. Barron
(74) *Attorney, Agent, or Firm* — Gene J. Yao; Barnes & Thornburg LLP

(57) ABSTRACT

Method for suppressing bone cancer-induced allodynia in a patient, the method comprising administration of a therapeutically effective amount of a non-cytotoxic protease to a patient suffering from bone cancer.

18 Claims, 4 Drawing Sheets

FIG. 4

SUPPRESSION OF BONE CANCER-INDUCED ALLODYNIA

This application is a U.S. national stage filing of International Patent Application No. PCT/EP2019/063069, filed May 21, 2019, which claims the priority of European Application No. 18173441.9, filed May 21, 2018.

The present invention relates to a method for suppressing bone cancer-induced allodynia, preferably for suppressing tactile allodynia induced by bone cancer.

Allodynia means "other pain." It is a pain that results from a stimulus that is not normally painful. By way of example, a subject suffering from bad sunburn may experience intense pain even to light touch. In more detail, sun exposure can overly sensitize the skin such that wearing a shirt or taking a shower can be very painful. Thus, a sufferer of tactile allodynia (aka static tactile allodynia or mechanical allodynia) may experience pain to touch, such as with resting one's head on a pillow, or with wearing a hat, earrings, or necklace. Similarly, a sufferer of dynamic allodynia may experience pain from lightly brushing one's hair, or from shaving one's face. Allodynia is a condition that is distinct from "referred" pain (also known as reflective pain), although it can occur outside the area stimulated. It is also distinct from hyperalgesia, which is a pain stimulus that is more painful than usual. Indeed, as mentioned above, allodynia is by it very definition "pain due to a stimulus that does not usually provoke pain", as opposed to hyperalgesia (increased pain from a stimulus that does usually provoke pain).

Allodynia is distinct from "referred" pain and hyperalgesia not only at the symptomatic level, but also at the molecular/cellular level. It is known that peripheral sensitisation and maladaptive central changes contribute to the generation and maintenance of reactions to a sensory modality (e.g. touch, pressure, pinprick, cold, and heat), with separate mechanisms in different subtypes of allodynia and hyperalgesia. The underlying mechanism of "cutaneous allodynia" in migraine has been reported to be due to sensitization of specific set of neurons, namely second-order neurons in the trigeminal nucleus caudalis (TNC).

A difference between allodynia and other types of pain is demonstrated by the fact that certain analgesics are not efficacious for the treatment of allodynia. For example, it has been reported that allodynia shows poor response to the triptans (a class of drug which act as agonists for serotonin 5-HT1B and 5-HT1 D receptors at blood vessels and nerve endings in the brain), suggesting that allodynia is not (or is poorly) associated with said receptors, such that they are poor candidate targets for an allodynia treatment.

Allodynia is associated (e.g. induced by) with certain disorders, notably bone cancer. Approximately one third of patients with an advanced cancer develop clinically relevant skeletal metastases during the course of their disease. This is most prominent in patients suffering from breast, prostate or lung cancer. Indeed, bone is the third most common site of metastases after the lung and liver.

Generally, bone metastases appear with an advanced stage of malignancies and are associated with pain (cancer-induced bone pain). Bone pain is a major clinical problem associated with impaired functional outcomes and poor quality of life. In both osteolytic and osteoblastic metastatic bone cancer sufferers, pain results from structural damage of the bone, periosteal irritation and nerve entrapment. Pain is usually described as a deep, boring, localised sensation that aches and burns in a compromised area, and typically becomes exacerbated by weight bearing. Mechanical allodynia is particularly prevalent in metastatic bone cancer, causing intense pain during coughing, turning in bed, or gentle limb movements.

Opioid management of advanced bone cancer pain (e.g. allodynia) is common, and reasonably efficacious. However, the dose range required to attenuate bone cancer pain produces unacceptable cognitive and gastro-intestinal side effects, and there exist many patient-types for which opioids are contraindicated (see below). In addition, the now widely acknowledged problem of opioid-dependence casts serious doubts over the future use (especially the long-term use) of this class of drug as a suitable analgesic of choice.

Accordingly, there is an increasing need for alternative anti-allodynia therapies/therapeutics. In particular, there is a need for alternative analgesics effective in suppressing bone cancer-induced pain.

The present invention addresses this problem by providing an alternative and/or improved means for suppressing bone cancer-induced allodynia.

The present invention is predicated on the surprising finding that administration of a non-cytotoxic protease leads to suppression of allodynia. This is surprising, given the unique molecular nature of allodynia compared with e.g. neuralgia (for which non-cytotoxic proteases have traditionally been used).

Further to this finding, the present inventors have found that a non-cytotoxic protease leads to suppression of a particularly uncomfortable (e.g. associated with a significant decrease in the quality of life) type of allodynia, namely bone-cancer induced allodynia. Thus, the present inventors have identified an important subpopulation (or subgroup) of patients which can benefit from treatment with a non-cytotoxic protease.

Thus, not only have the present inventors discovered a new field of use for a non-cytotoxic protease (allodynia), they have discovered a surprising technical effect with said field (suppression of bone-cancer induced allodynia).

Accordingly, the present invention provides a method for suppressing bone cancer-induced allodynia in a patient, said method comprising administration of a therapeutically effective amount of a non-cytotoxic protease to a patient suffering from bone cancer.

The present invention provides a corresponding therapeutic use, namely a non-cytotoxic protease for use in suppressing bone cancer-induced allodynia in a patient suffering from bone cancer.

In a key advantage of the invention, the present invention provides an advantageous 're-purposing' of a non-cytotoxic protease, providing alternative treatment to addictive analgesics such as opioids (e.g. morphine). This is particularly advantageous for treating patients for which another (different) pain medicine is contraindicated—by way of example, all triptans are contraindicated in patients with cardiovascular diseases (coronary spasms, symptomatic coronary artery disease, after a heart attack or stroke, uncontrolled hypertension, Raynaud's disease, peripheral artery disease). Most triptans are also contraindicated during pregnancy and breastfeeding and for patients younger than 18. There exist numerous contraindications to opioids (morphine), such as (simply by way of example) systemic mastocytosis, untreated decreased level of thyroid hormones, and decreased function of the adrenal gland.

In one embodiment, the non-cytotoxic protease is administered to a subject. The terms "subject", "individual" and "patient" are used interchangeably herein to refer to a mammalian subject. In one embodiment the "subject" is a human, a companion animal (e.g. a pet such as a dog, cat, and/or rabbit), livestock (e.g. a pig, sheep, cattle, and/or a goat), and/or a horse. In one embodiment, the subject (patient) is a human.

In methods of the invention, the subject may not have been previously diagnosed as having a bone cancer. Alternatively, the subject may have been previously diagnosed as having a bone cancer. The subject may also be one who exhibits disease risk factors, or one who is asymptomatic for a bone cancer. The subject may also be one who is suffering from or is at risk of developing a bone cancer. In one embodiment, the subject has been previously administered a therapy for a bone cancer.

In methods of the invention, the subject may not have been previously diagnosed as having a bone cancer-induced allodynia. Alternatively, the subject may have been previously diagnosed as having a bone cancer-induced allodynia. The subject may also be one who exhibits disease risk factors, or one who is asymptomatic for a bone cancer-induced allodynia. The subject may also be one who is suffering from or is at risk of developing a bone cancer-induced allodynia. In one embodiment, the subject has been previously administered a therapy for a bone cancer-induced allodynia.

The term "suppressing" is used synonymously with the term "treating" herein. Thus, the present invention embraces a method for treating bone cancer-induced allodynia in a patient, said method comprising administration of a therapeutically effective amount of a non-cytotoxic protease to a patient suffering from bone cancer. The present invention also embraces a corresponding therapeutic use, namely a non-cytotoxic protease for use in treating bone cancer-induced allodynia in a patient suffering from bone cancer.

The term "suppress" or "suppressing", or "treat" or "treating" as used herein encompasses prophylactic suppression and treatment (e.g. to prevent onset of bone cancer-induced allodynia) as well as corrective suppression and treatment (suppression and treatment of a subject already suffering from bone cancer-induced allodynia). In a preferable embodiment, the term "suppress" or "suppressing" as used herein means corrective treatment. In a preferable embodiment, the term "treat" or "treating" as used herein means corrective treatment. The term suppress" or "suppressing", or "treat" or "treating" encompasses suppressing and treating both the bone cancer-induced allodynia and a symptom thereof. In some embodiments the term "suppress" or "suppressing", or "treat" or "treating" refers to a symptom of bone cancer-induced allodynia.

Therefore, a non-cytotoxic protease and/or analgesic molecule (preferably non-cytotoxic protease) may be administered to a subject in a therapeutically effective amount or a prophylactically effective amount.

A "therapeutically effective amount" is any amount of the non-cytotoxic protease and/or analgesic molecule (preferably non-cytotoxic protease), which when administered alone or in combination to a subject for suppressing/treating a bone cancer-induced allodynia (or a symptom thereof) is sufficient to effect such suppression/treatment of the bone cancer-induced allodynia, or symptom thereof.

A "prophylactically effective amount" is any amount of the non-cytotoxic protease and/or analgesic molecule (preferably non-cytotoxic protease) that, when administered alone or in combination to a subject inhibits or delays the onset or reoccurrence of a bone cancer-induced allodynia (or a symptom thereof). In some embodiments, the prophylactically effective amount prevents the onset or reoccurrence of a bone cancer-induced allodynia entirely. "Inhibiting" the onset means either lessening the likelihood of bone cancer-induced allodynia onset (or symptom thereof), or preventing the onset entirely.

In one embodiment, methods and uses of the invention comprise one or more administration step selected from oral, intravenous, intraarterial, intraperitoneal, intramuscular, subcutaneous, rectal, or vaginal, inhalation, topical, or a combination thereof. In one embodiment, the administration is one or more selected from intravenous, intraarterial (e.g. by injection or drip), subcutaneous, or a combination thereof.

In one embodiment, said method/therapeutic use includes co-administration of an analgesic (e.g. an opiate such as morphine). Therefore, the invention provides a therapeutic combination comprising a non-cytotoxic protease component and an opioid component. The analgesic is distinct from the non-cytotoxic protease component, and is preferably administered in a sub-efficacious therapeutically effect amount. Said combination therapy achieves an unexpected analgesic effect, and reduces the opioid component therapeutic burden.

The order of application/administration of the component parts of the therapeutic combination can be varied. The non-cytotoxic protease and the opioid can be administered simultaneously (e.g. both at their own particular optimal dose for achieving synergy), either as part of a single composition or within separate compositions. For example, the non-cytotoxic protease may be present in a first composition (e.g. adapted for intravenous administration to a subject) and the opioid may be present in a second composition (e.g. adapted for intravenous, subcutaneous or oral administration to a subject).

Furthermore, the non-cytotoxic protease and the opioid may be administered at different times (e.g. a non-cytotoxic protease may be pre-administered to sensitise a bone cancer-induced allodynia to an opioid, and vice versa). Thus, in a further embodiment a non-cytotoxic protease and an opioid are administered to a subject at different times, within separate compositions.

In one embodiment a non-cytotoxic protease component is administered prior to an opioid. In one embodiment a non-cytotoxic protease component is administered simultaneously with an opioid. In one embodiment a non-cytotoxic protease is administered sequentially to an opioid.

Thus, in use, the non-cytotoxic protease component may be administered prior to, simultaneously with, or subsequent to the different analgesic component.

In one embodiment, the allodynia is one or more selected from tactile allodynia (used synonymously with the term "mechanical allodynia"), static allodynia (e.g. pain in response when touched), dynamic allodynia (e.g. pain in response to stroking lightly), thermal (hot or cold) allodynia (e.g. pain from normally mild skin temperatures in the affected area), movement allodynia (e.g. pain triggered by normal movement of joints or muscles) or cutaneous allodynia.

In one embodiment, the allodynia consists of or comprises tactile allodynia (aka static tactile allodynia or mechanical allodynia) and/or dynamic allodynia. In a preferable embodiment, the allodynia is tactile allodynia (e.g. mechanical allodynia).

Administration is typically local to a site selected from a structurally damaged bone, a periosteal irritation, a nerve entrapment, and/or other compromised area. Administration is typically proximal to a local concentration of bone cancer cells.

In one embodiment, administration is direct into the bone cancer cells or into connective tissue thereof.

Without wishing to be bound by theory, it is believed that allodynia is more likely to be induced by a metastatic cancer (e.g. more so than a benign and/or non-, metastatic cancer). Another theory posits that allodynia is more likely to be induced by a metastatic cancer arising from a different (e.g. non-bone) tissue, before metastasising to the bone (e.g. due to invasion of surrounding soft tissue violations).

In one embodiment, the bone cancer is a metastatic bone cancer (e.g. bone metastasis).

In one embodiment, the bone cancer is a metastatic cancer that arises from a tissue other than bone (e.g. a tissue that is distinct from bone tissue). Examples of tissues where the cancer may arise (before metastasising to the bone) include tissue of the prostate, breast, lung, and/or ovary.

In one embodiment, the patient (e.g. subject) has one from one or more cancer (preferably further to said bone cancer) selected from a lung cancer, a breast cancer, a prostate cancer, and an ovarian cancer (preferably a metastatic lung cancer, a metastatic breast cancer, a metastatic prostate cancer, and a metastatic ovarian cancer). The patient may have a lung cancer. The patient may have a breast cancer. The patient may have a prostate cancer. The patient may have an ovarian cancer.

In one embodiment, the bone cancer is a metastatic cancer that is distinct from a benign tumour. In one embodiment, the allodynia is not induced by an Osteoid Osteoma. In one embodiment, the bone cancer is distinct from Osteoid Osteoma (i.e. the bone cancer does not comprise an Osteoid Osteoma).

An assessment of said "suppression of bone-cancer induced allodyna", is demonstrated by reference to the accompanying Examples, and may be assessed using the methodology described in the Examples (e.g. Example 1). For example, Example 1 (and the associated Materials and Methods) describes a method for measuring allodynia using the electronic Von Frey test. This test involves the application of an increasing pressure onto the plantar aspect of the hind paws of an animal (preferably a rat). The test is employed on animals with one hind paw inflamed by an injection or injured, and one normal hind paw (e.g. control paw), to evaluate a candidate agent (e.g. non-cytotoxic protease) that has been administered to the animal for analgesic action. The apparatus exerts a steadily increasing force and reaction thresholds are determined as the pressure (g) required to elicit paw withdrawal, to provide an observed "Paw Withdrawal Threshold (g)" value.

The animal utilised in the electronic von Frey test is preferably the MRMT-1 mammary carcinoma cells model of bone cancer pain in rats (Medhurst S. J., et al., "*A rat model of bone cancer*", Pain, 2002: pp. 129-140; incorporated herein by reference), a well characterized animal model for pharmaceutical testing in cancer pain. This model is a widely accepted model as it mimics aspects of pathogenesis and pathology in a period of time compatible with preclinical pain studies.

Said "Paw Withdrawal Threshold (g)" may be measured at one or more selected from 2 days, 4 days, 6 days, 8 days, 10 days, 12 days, 14 days, 15 days, 16 days, 17 days, 18 days, 19 days, 20 days, or 21 days post treatment with the non-cytotoxic protease. In one embodiment, the "Paw Withdrawal Threshold (g)" may be measured at one or more selected from 14 days, 18 days, or 21 days (preferably 21 days) post treatment with the non-cytotoxic protease and/or injuring the paw of the animal. Preferably, a pre-treatment measurement is also taken before inflaming or injuring the paw.

In one embodiment, said "Paw Withdrawal Threshold (g)" may be measured at one or more selected from 0 min, 30 min, 60 min, 90 min, 120 min, 150 min, 140 min, and 160 min (preferably 160 min) post treatment with the non-cytotoxic protease and/or injuring the paw of the animal. Preferably, a pre-treatment measurement is also taken before inflaming or injuring the paw.

In one embodiment, a non-cytotoxic protease of the invention suppresses a bone cancer-induced allodynia by at least 10%, or at least 20%, or at least 30%, or at least 40%, or at least 50%, or at least 60%, or at least 70%, or at least 80%, or at least 90% or by 100% (corresponding to an increase in the "Paw Withdrawal Threshold" by at least 10%, or at least 20%, or at least 30%, or at least 40%, or at least 50%, or at least 60%, or at least 70%, or at least 80%, or at least 90% or 100%) greater that an otherwise identical administration lacking a non-cytotoxic protease (e.g. a vehicle-only administration).

In one embodiment, a non-cytotoxic protease of the invention suppresses a bone cancer-induced allodynia by at least 2%, or at least 4%, or at least 6%, or at least 8%, or at least 10%, or at least 12%, or at least 14%, or at least 16%, or at least 18% or by 20% (corresponding to an increase in the "Paw Withdrawal Threshold" by at least 2%, or at least 4%, or at least 6%, or at least 8%, or at least 10%, or at least 12%, or at least 14%, or at least 16%, or at least 18% or by 20%) greater that an otherwise identical administration lacking a non-cytotoxic protease (e.g. a vehicle-only administration).

In contrast to a cytotoxic protease (e.g. ricin, diphtheria toxin, *pseudomonas* exotoxin), which acts by killing its natural target cell, a non-cytotoxic protease acts by transiently incapacitating the cellular function of its natural target cell. Importantly, a non-cytotoxic protease does not kill the natural target cell upon which it acts. Some of the best known examples of non-cytotoxic proteases include clostridial neurotoxins (e.g. botulinum neurotoxin, which is marketed under names such as Dysport™, Neurobloc™, and Botox™), IgA proteases (see, for example, WO99/032272), and antarease proteases (see, for example, WO2011/022357). In more detail, non-cytotoxic proteases act by proteolytically-cleaving and thus inactivating intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are essential components of the vesicular secretion process in eukaryotic cells. Thus, non-cytotoxic proteases act by suppressing cellular secretion. This class of protein includes re-targeted non-cytotoxic proteins in which the natural binding ability of the protein has been modified by the introduction of a binding ligand (also known as a Targeting Moiety), thereby conferring new target cell binding properties on the modified protein. Applicant has pioneered the technology relating to the re-targeting of non-cytotoxic proteases, which dates back to the 1990s (see, for example, WO 94/21300, WO 96/33273 and WO 98/07864). Said re-targeted proteins are referred to (throughout the literature and scientific community) as Targeted Secretion Inhibitors (TSIs)—reference to TSIs includes structural equivalents such as those described in WO 2011/018665.

A preferred non-cytotoxic protease of the present invention is a clostridial neurotoxin such as tetanus toxin, a botulinum neurotoxin (e.g. BoNT/A, BoNT/B, BONT/C1, BoNT/D, BoNT/E, BoNT/F, BoNT/G, and sub-types thereof), or C. butyricum. In a preferable embodiment, the non-cytotoxic protease is BoNT/A.

Reference herein to a non-cytotoxic protease includes natural and recombinant clostridial neurotoxin proteases, antarease proteases, and IgA proteases. This embraces serotype hybrids (such as BoNT structural domain serotype hybrids), and modified neurotoxins (such as TSIs), and multi-domain neurotoxins (e.g. multi L-chain BoNTs).

A non-cytotoxic protease of the present invention effects the same sequential intoxication steps that a clostridial neurotoxin is able to demonstrate (see FIG. 4). For example, binding to the natural target cell of a clostridial neurotoxin, leading to endosomal release of the non-cytotoxic protease into the cytosol of said target cell, and resulting in SNARE cleavage within the cytosol. In a preferred embodiment, a non-cytotoxic protease of the present invention effects the same sequential intoxication steps that a BoNT/A (e.g. BoNT/Aˆ is able to demonstrate, namely binding to nerve cells (e.g. via polysialoganglioside receptor) of the presynaptic muscular junction, leading to endosomal release of the protease into the cytosol, and resulting in SNAP-25 cleavage within the cytosol.

By way of example, typical protease (reference) sequences include:

| Botulinum type A neurotoxin | amino acid residues (1-448) |
| Botulinum type B neurotoxin | amino acid residues (1-440) |
| Botulinum type C neurotoxin | amino acid residues (1-441) |
| Botulinum type D neurotoxin | amino acid residues (1-445) |
| Botulinum type E neurotoxin | amino acid residues (1-422) |
| Botulinum type F neurotoxin | amino acid residues (1-439) |
| Botulinum type G neurotoxin | amino acid residues (1-441) |
| Tetanus neurotoxin | amino acid residues (1-457) |
| IgA protease | amino acid residues (1-959)* |

*Pohlner, J. et al. (1987). Nature 325, pp. 458-462, which is hereby incorporated by reference thereto.

The above-identified reference sequence should be considered a guide as slight variations may occur according to sub-serotypes. By way of example, US 2007/0166332 (hereby incorporated by reference thereto) cites slightly different clostridial sequences:

| Botulinum type A neurotoxin | amino acid residues (M1-K448) |
| Botulinum type B neurotoxin | amino acid residues (M1-K441) |
| Botulinum type C neurotoxin | amino acid residues (M1-K449) |
| Botulinum type D neurotoxin | amino acid residues (M1-R445) |
| Botulinum type E neurotoxin | amino acid residues (M1-R422) |
| Botulinum type F neurotoxin | amino acid residues (M1-K439) |
| Botulinum type G neurotoxin | amino acid residues (M1-K446) |
| Tetanus neurotoxin | amino acid residues (M1-A457) |

A variety of clostridial toxin fragments comprising the light chain can be useful in aspects of the present invention with the proviso that these light chain fragments can specifically target the core components of the neurotransmitter release apparatus and thus participate in executing the overall cellular mechanism whereby a clostridial toxin proteolytically cleaves a substrate. The light chains of clostridial toxins are approximately 420-460 amino acids in length and comprise an enzymatic domain. Research has shown that the entire length of a clostridial toxin light chain is not necessary for the enzymatic activity of the enzymatic domain. As a non-limiting example, the first eight amino acids of the BoNT/A light chain are not required for enzymatic activity. As another non-limiting example, the first eight amino acids of the TeNT light chain are not required for enzymatic activity. Likewise, the carboxyl-terminus of the light chain is not necessary for activity. As a non-limiting example, the last 32 amino acids of the BoNT/A light chain (residues 417-448) are not required for enzymatic activity. As another non-limiting example, the last 31 amino acids of the TeNT light chain (residues 427-457) are not required for enzymatic activity. Thus, aspects of this embodiment can include clostridial toxin light chains comprising an enzymatic domain having a length of, for example, at least 350 amino acids, at least 375 amino acids, at least 400 amino acids, at least 425 amino acids and at least 450 amino acids. Other aspects of this embodiment can include clostridial toxin light chains comprising an enzymatic domain having a length of, for example, at most 350 amino acids, at most 375 amino acids, at most 400 amino acids, at most 425 amino acids and at most 450 amino acids.

In one embodiment, the non-cytotoxic protease cleaves a non-neuronal SNARE protein such as a SNAP-23 protein. In one embodiment, the non-cytotoxic protease is a modified botulinum toxin L-chain capable of cleaving SNAP-23. An example of such a modified L-chain is described by Chen and Barbieri, PNAS, vol. 106, no. 23, p 91 80-91 84, 2009.

In one embodiment, the non-cytotoxic protease is a BoNT/A, BoNT/C or BoNT/E protease, and the preferred SNARE motif is a SNAP (e.g. SNAP 25) motif. In another embodiment, the non-cytotoxic protease is a BoNT/B, BoNT/D, BoNT/F or BoNT/G or tetanus neurotoxin (TeNT) protease, and the preferred SNARE motif is a VAMP motif. In another embodiment, the non-cytotoxic protease is a BoNT/C1 protease, and the preferred SNARE motif is a syntaxin motif.

The polypeptides of the present invention, especially the protease component thereof, may be PEGylated—this may help to increase stability, for example duration of action of the protease component. PEGylation is particularly preferred when the protease comprises a BoNT/A, B or C1 protease. PEGylation preferably includes the addition of PEG to the N-terminus of the protease component. By way of example, the N-terminus of a protease may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is incorporated in its entirety by reference thereto.

The non-cytotoxic protease is preferably a BoNT/A, BoNT/C-i or BoNT/E protease, and the preferred SNARE motif is a SNAP (e.g. SNAP 25) motif.

Alternatively, the non-cytotoxic protease may be a BoNT/B, BoNT/D, BoNT/F or BoNT/G or tetanus neurotoxin (TeNT) protease, and the preferred SNARE motif is a VAMP motif. Alternatively, the non-cytotoxic protease is a BONT/C1 protease, and the preferred SNARE motif is a syntaxin motif.

In use, the non-cytotoxic protease of the present invention (eg. the L-chain of a clostridial neurotoxin, or equivalent SNARE-cleaving protease) is typically delivered to its target location (i.e. the cytosol of the natural target cell of a clostridial neurotoxin) by cooperation/coordination with clostridial neurotoxin scaffold components, namely a Targeting Moiety (eg. the He domain of a clostridial neurotoxin, or equivalent) and a Translocation Domain (eg. the HN domain of a clostridial neurotoxin, or equivalent). These scaffold components are well known to a person of skill in the art.

By way of example, typical translocation (reference) sequences include:

| | |
|---|---|
| Botulinum type A neurotoxin | amino acid residues (449-871) |
| Botulinum type B neurotoxin | amino acid residues (441-858) |
| Botulinum type C neurotoxin | amino acid residues (442-866) |
| Botulinum type D neurotoxin | amino acid residues (446-862) |
| Botulinum type E neurotoxin | amino acid residues (423-845) |
| Botulinum type F neurotoxin | amino acid residues (440-864) |
| Botulinum type G neurotoxin | amino acid residues (442-863) |
| Tetanus neurotoxin | amino acid residues (458-879) |

The above-identified reference sequence should be considered a guide as slight variations may occur according to sub-serotypes. By way of example, US 2007/0166332 (hereby incorporated by reference thereto) cites slightly different clostridial sequences:

| | |
|---|---|
| Botulinum type A neurotoxin | amino acid residues (A449-K871) |
| Botulinum type B neurotoxin | amino acid residues (A442-S858) |
| Botulinum type C neurotoxin | amino acid residues (T450-N866) |
| Botulinum type D neurotoxin | amino acid residues (D446-N862) |
| Botulinum type E neurotoxin | amino acid residues (K423-K845) |
| Botulinum type F neurotoxin | amino acid residues (A440-K864) |
| Botulinum type G neurotoxin | amino acid residues (S447-S863) |
| Tetanus neurotoxin | amino acid residues (S458-V879) |

The present invention also embraces variant translocation domains, so long as the variant domains still demonstrate the requisite translocation activity. By way of example, a variant may have at least 70%, preferably at least 80%, more preferably at least 90%, and most preferably at least 95% or at least 98% amino acid sequence homology with a reference translocation domain. The term fragment, when used in relation to a translocation domain, means a peptide having at least 20, preferably at least 40, more preferably at least 80, and most preferably at least 100 amino acid residues of the reference translocation domain. In the case of a clostridial translocation domain, the fragment preferably has at least 100, preferably at least 150, more preferably at least 200, and most preferably at least 250 amino acid residues of the reference translocation domain (eg. $H_N$ domain). As with the TM 'fragment' component (discussed above), translocation 'fragments' of the present invention embrace fragments of variant translocation domains based on the reference sequences.

It is well documented that certain domains of bacterial toxin molecules are capable of forming such pores. It is also known that certain translocation domains of virally expressed membrane fusion proteins are capable of forming such pores. Such domains may be employed in the present invention.

Other examples include the translocation domain of diphtheria toxin, the translocation domain of *Pseudomonas* exotoxin type A, the translocation domains of anthrax toxin, influenza virus haemagglutinin, Semliki Forest virus fusogenic protein, Vesicular Stomatitis virus glycoprotein G, SER virus F protein, and Foamy virus envelope glycoprotein.

In the context of the present invention, a variety of clostridial toxin $H_N$ regions comprising a translocation domain can be useful in aspects of the present invention with the proviso that these active fragments can facilitate the release of a non-cytotoxic protease (e.g. a clostridial L-chain) from intracellular vesicles into the cytoplasm of the target cell and thus participate in executing the overall cellular mechanism whereby a clostridial toxin proteolytically cleaves a substrate. The $H_N$ regions from the heavy chains of Clostridial toxins are approximately 410-430 amino acids in length and comprise a translocation domain. Research has shown that the entire length of a $H_N$ region from a Clostridial toxin heavy chain is not necessary for the translocating activity of the translocation domain. Thus, aspects of this embodiment can include clostridial toxin HN regions comprising a translocation domain having a length of, for example, at least 350 amino acids, at least 375 amino acids, at least 400 amino acids and at least 425 amino acids. Other aspects of this embodiment can include clostridial toxin $H_N$ regions comprising translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, we refer to Henderson et al (1997) in The Clostridia: Molecular Biology and Pathogenesis, Academic press. The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin. Examples of non-clostridial (reference) Translocation Domain origins include, but not be restricted to, the translocation domain of diphtheria toxin [O'Keefe et ah, Proc. Natl. Acad. Sci. USA (1992) 89, 6202-6206; Silverman et ah, J. Biol. Chem. (1993) 269, 22524-22532; and London, E. (1992) Biochem. Biophys. Acta., 1112, pp. 25-51], the translocation domain of *Pseudomonas* exotoxin type A [Prior et ah Biochemistry (1992) 31, 3555-3559], the translocation domains of anthrax toxin [Blanke et ah Proc. Nath Acad. Sci. USA (1996) 93, 8437-8442], a variety of fusogenic or hydrophobic peptides of translocating function [Plank et ah J. Biol. Chem. (1994) 269, 12918-12924; and Wagner et al (1992) PNAS, 89, pp. 7934-7938], and amphiphilic peptides [Murata et al (1992) Biochem., 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral (reference) Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E 1 protein of SFV and the G protein of the G protein of VSV.

Use of the (reference) Translocation Domains includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

The polypeptides of the present invention may further comprise a translocation facilitating domain. Said domain facilitates delivery of the non-cytotoxic protease into the cytosol of the target cell and are described, for example, in WO 08/008803 and WO 08/008805, each of which is herein incorporated by reference thereto.

By way of example, suitable translocation facilitating domains include an enveloped virus fusogenic peptide domain, for example, suitable fusogenic peptide domains include influenzavirus fusogenic peptide domain (eg. influenza A virus fusogenic peptide domain of 23 amino acids), alphavirus fusogenic peptide domain (eg. Semliki Forest virus fusogenic peptide domain of 26 amino acids), vesiculovirus fusogenic peptide domain (eg. vesicular stomatitis virus fusogenic peptide domain of 21 amino acids), respirovirus fusogenic peptide domain (eg. Sendai virus fusogenic peptide domain of 25 amino acids), morbiliivirus fusogenic peptide domain (eg. Canine distemper virus fusogenic peptide domain of 25 amino acids), avulavirus fusogenic peptide domain (eg. Newcastle disease virus fusogenic peptide domain of 25 amino acids), henipavirus fusogenic peptide domain (eg. Hendra virus fusogenic peptide domain of 25 amino acids), metapneumovirus fusogenic peptide domain (eg. Human metapneumovirus fusogenic peptide domain of 25 amino acids) or spumavirus fusogenic peptide domain such as simian foamy virus fusogenic peptide domain; or fragments or variants thereof.

By way of further example, a translocation facilitating domain may comprise a Clostridial toxin $H_CN$ domain or a fragment or variant thereof. In more detail, a Clostridial toxin $H_CN$ translocation facilitating domain may have a length of at least 200 amino acids, at least 225 amino acids, at least 250 amino acids, at least 275 amino acids. In this regard, a Clostridial toxin HCN translocation facilitating domain preferably has a length of at most 200 amino acids, at most 225 amino acids, at most 250 amino acids, or at most 275 amino acids. Specific (reference) examples include:

| | |
|---|---|
| Botulinum type A neurotoxin | amino acid residues (872-1 110) |
| Botulinum type B neurotoxin | amino acid residues (859-1097) |
| Botulinum type C neurotoxin | amino acid residues (867-1 111) |
| Botulinum type D neurotoxin | amino acid residues (863-1098) |
| Botulinum type E neurotoxin | amino acid residues (846-1085) |
| Botulinum type F neurotoxin | amino acid residues (865-1 105) |
| Botulinum type G neurotoxin | amino acid residues (864-1 105) |
| Tetanus neurotoxin | amino acid residues (880-1 127) |

The above sequence positions may vary a little according to serotype/sub-type, and further examples of suitable (reference) Clostridial toxin $H_CN$ domains include:

| | |
|---|---|
| Botulinum type A neurotoxin | amino acid residues (874-1 110) |
| Botulinum type B neurotoxin | amino acid residues (861-1097) |
| Botulinum type C neurotoxin | amino acid residues (869-1 111) |
| Botulinum type D neurotoxin | amino acid residues (865-1098) |
| Botulinum type E neurotoxin | amino acid residues (848-1085) |
| Botulinum type F neurotoxin | amino acid residues (867-1 105) |
| Botulinum type G neurotoxin | amino acid residues (866-1 105) |
| Tetanus neurotoxin | amino acid residues (882-1 127) |

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a Clostridial toxin $H_CN$ translocation facilitating domain may be combined with a non-clostridal translocation domain peptide. Alternatively, a Clostridial toxin $H_CN$ facilitating domain may be combined or with a clostridial translocation domain peptide, examples of which include:

| | |
|---|---|
| Botulinum type A neurotoxin | amino acid residues (449-1 110) |
| Botulinum type B neurotoxin | amino acid residues (442-1097) |
| Botulinum type C neurotoxin | amino acid residues (450-1 111) |
| Botulinum type D neurotoxin | amino acid residues (446-1098) |
| Botulinum type E neurotoxin | amino acid residues (423-1085) |
| Botulinum type F neurotoxin | amino acid residues (440-1 105) |
| Botulinum type G neurotoxin | amino acid residues (447-1 105) |
| Tetanus neurotoxin | amino acid residues (458-1 127) |

By way of example, typical Targeting Moiety (reference) sequences include:

| | |
|---|---|
| Botulinum type A neurotoxin | amino acid residues (Y1 111-L1296) |
| Botulinum type B neurotoxin | amino acid residues (Y1098-E1291) |
| Botulinum type C neurotoxin | amino acid residues (Y1 112-E1291) |
| Botulinum type D neurotoxin | amino acid residues (Y1099-E1276) |
| Botulinum type E neurotoxin | amino acid residues (Y1086-K1252) |
| Botulinum type F neurotoxin | amino acid residues (Y1 106-E1274) |
| Botulinum type G neurotoxin | amino acid residues (Y1 106-E1297) |
| Tetanus neurotoxin | amino acid residues (Y1 128-D1 3 15). |

The non-cytotoxic protease may be administered at a dose of 1-100 U/kg patient, preferably at a dose of 10-50 U/kg patient.

For example, the non-cytotoxic protease may be administered at a dose of one or more selected from 5 U/kg, 10 U/kg, 20 U/kg, or 40 U/kg (preferably 40 U/kg).

In one embodiment, the non-cytotoxic protease is administered as a single dose administration within a period of at least 2 months, preferably within a period of at least 3 months.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

| CONSERVATIVE AMINO ACID SUBSTITUTIONS | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a toxin" includes a plurality of such toxins and reference to "the toxin" includes reference to one or more toxins and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

Figure 4:
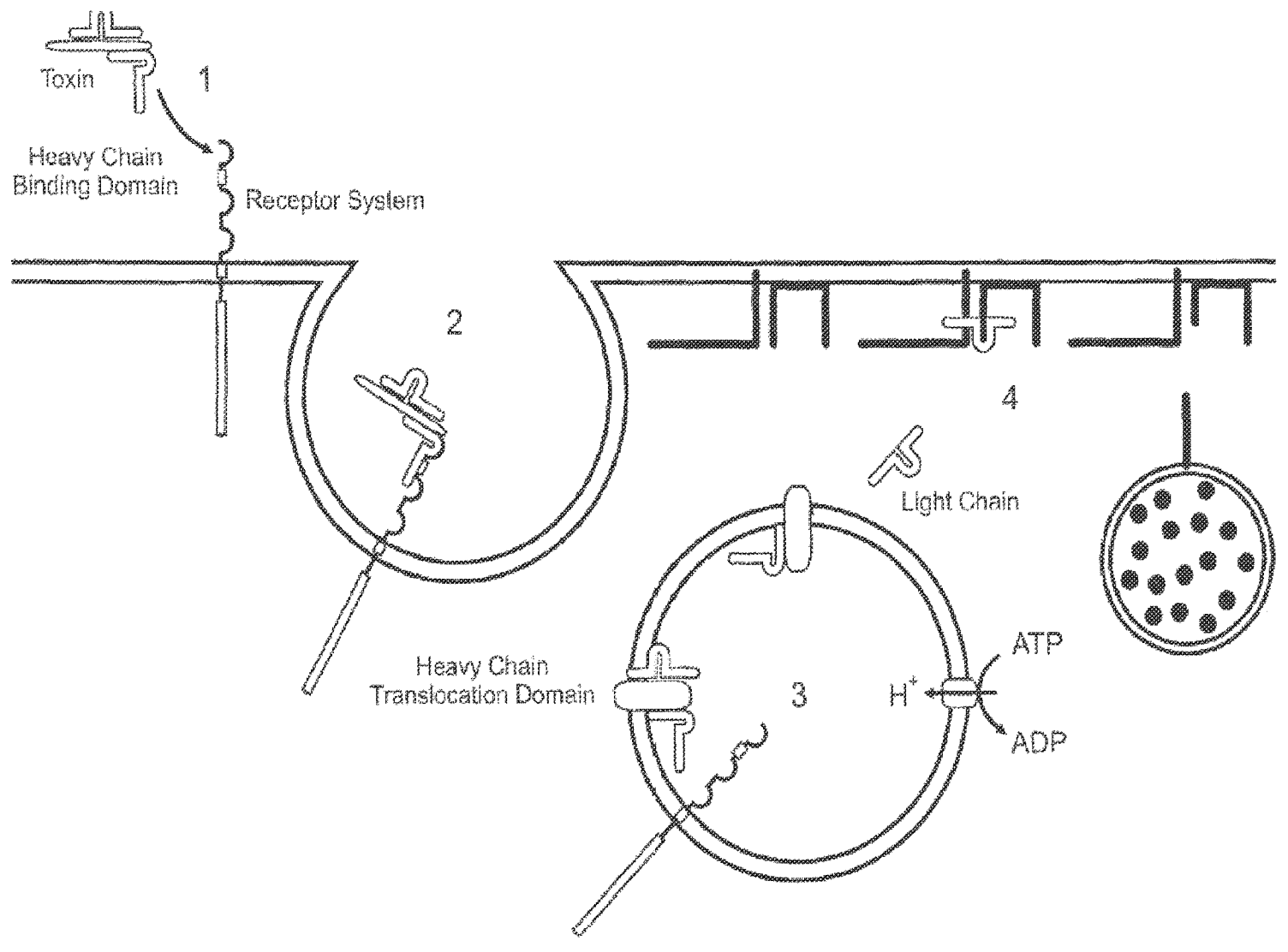

FIG. 4 shows the process of non-cytotoxic protease intoxication can be described as comprising four steps: 1) binding of non-cytotoxic protease via a binding domain (eg. via HC of a clostridial neurotoxin, or equivalent Targeting Moiety) to a Binding Site present on the cell surface; 2) the Binding Site (plus bound non-cytotoxic protease) becomes internalised into the cell 3) the non-cytotoxic protease effects release (eg. via HN of a clostridial neurotoxin, or equivalent Translocation Domain) from within the endosome and into the cytosol (i.e. the translocation event) 4) the released non-cytotoxic protease (eg. L-chain of a clostridial neurotoxin, or equivalent SNARE-cleaving protease) is able then to act on its intracellular (SNARE protein) target.

EXAMPLES

Figure 1:
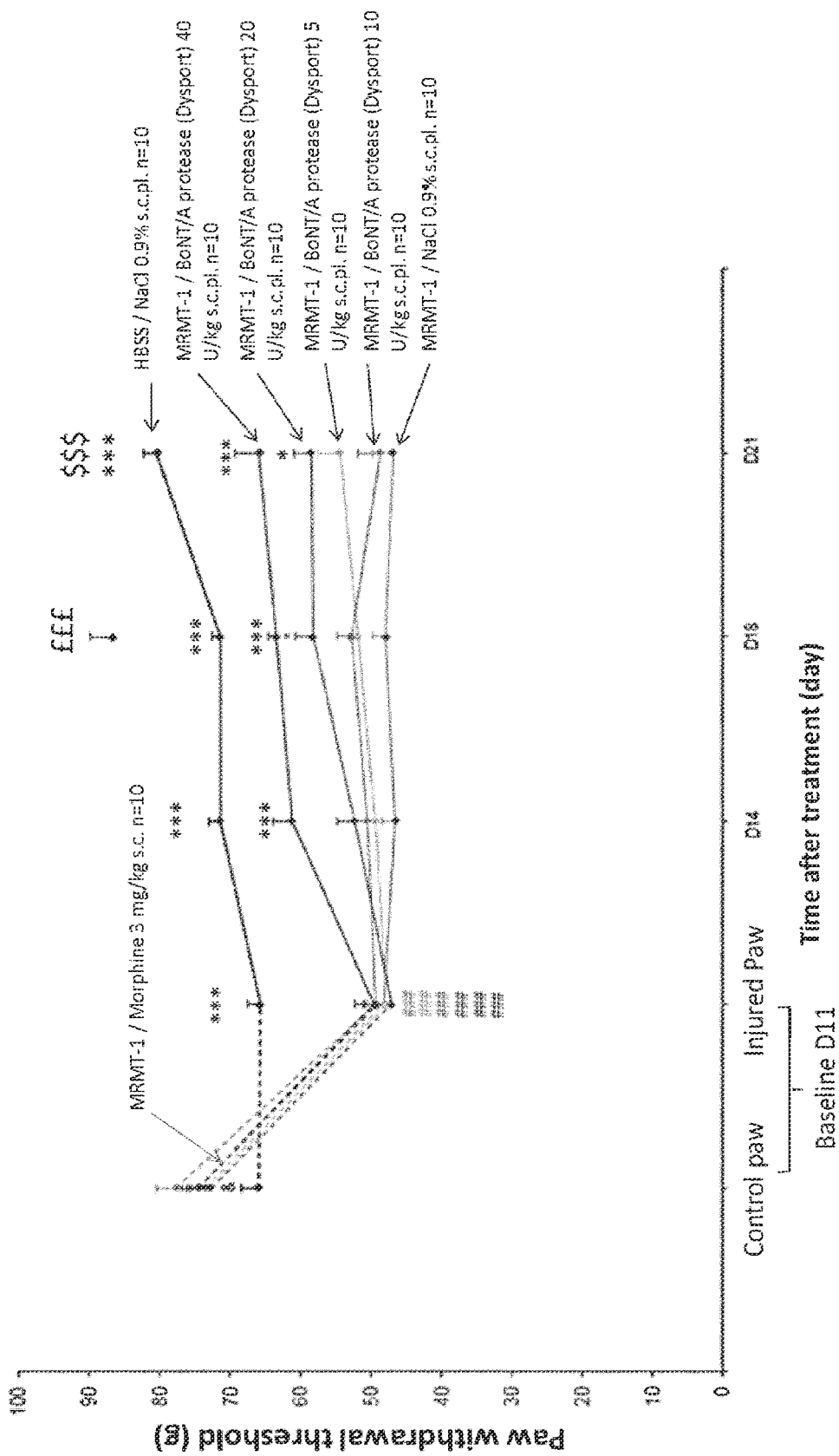
FIG. 1 shows BoNT/A protease (Dysport® 10-40 U/kg) dose-curve study, demonstrating the effect of a single intraplantar administration of BoNT/A protease as assessed in a rat model of MRMT-1 induced bone cancer pain.

The invention will now be described, by way of example only, with reference to the following Examples.

Materials and Methods

The MRMT-1 mammary carcinoma cells model of bone cancer pain in rats (Medhurst S. J., et al., "*A rat model of bone cancer*", Pain, 2002: pp. 129-140) is a well characterized animal model for pharmaceutical testing in cancer pain. This model is a widely accepted model as it mimics aspects of pathogenesis and pathology in a period of time compatible with preclinical pain studies.

Animals and Housing Conditions

Sixty (60) male Sprague-Dawley rats (SPF status, Janvier, France), weighing 175-200 g during the surgery were selected for these studies.

Rats were housed in a temperature (20-24° C.) and relative humidity (45%-65%) controlled room and acclimated to an artificial day/night cycle of 12 hours light (6.30 a.m. to 6.30 p.m.)/12 hours darkness. Rats had free access to tap water and were fed ad libitum with pelleted complete diet. Animals were housed 4 per cage (cages Type E) and acclimated for a period of at least 5 days before any testing. Each rat was identified by tail markings.

Reagents

Details of the non-cytotoxic protease use (BoNT/A Dysport®) are outlined in Table 1.

TABLE 1

| Non-cytotoxic protease | BoNT/A Dysport ® |
| --- | --- |
| Batch N°/Ipsen Bioinnovation | K02459 |
| Salified/unsalified ratio | 1.00 |
| Quantity/vial | 500 U |
| Description | Lyophilisate |
| Storage conditions | +4° C. (solution); −20° C. (Lyophilisate) |
| Specific formulation protocol | Solution in 0.9% NaCl |

Details of the reference substance (morphine) are outlined in Table 2, below.

TABLE 2

| Reference Substance ID | Morphine |
| --- | --- |
| Supplier | Francopia |
| Catalog reference | 3695 |
| Batch N° | IR00002 |
| Salified / unsalified | 1.13 |
| Storage conditions | RT |

Details on the vehicle used (e.g. for vehicle-only control experiments) are outlined in Table 3, below.

TABLE 3

| Vehicle ID | 0.9% NaCl |
| --- | --- |
| Source | Aguettant |
| Catalog reference | 069808 |
| Storage conditions | +4° C. |

0-9% NaCl employed as vehicle for the non-cytotoxic protease and for the morphine solution.

Details of the MRMT-1 cells, and HBSS are outlined in Table 4, below.

TABLE 4

| Reagent ID | MRMT-1 cells | HBSS |
| --- | --- | --- |
| Source | Pr. Sarret's laboratory, Department of Physiology and Biophysics, Universite de Sherbrooke, Sherbrooke, Quebec, Canada | Neuronax |
| Cells culture | Neuronax Facultés de Médecine et de Pharmacie, 5ème, 28, place Henri Dunant, 63000 Clermont-Ferrand, France | — |

Principal Equipment and Data Processing System

The Electronic von Frey (EVF3 model, Bioseb, France) was employed in pain tests (e.g. to assess tactile allodynia).

Analysis (e.g. statistical analysis) was conducted using the following tools:
  SigmaStat software version 3.5 (SPSS Science Software, Erkrath, Germany).
  Lab X direct software version 2.4 (Mettler Toledo, France).
  Dragon Naturally Speaking software version 13.0 (Nuance, France).

Pain Test

Tactile allodynia were assessed using the electronic Von Frey test. This test requires the application of an increasing pressure onto the plantar aspect of the hind paws. The test was employed on animals with one hind paw inflamed by an injection or injured, and one normal hind paw, to evaluate drugs for analgesic action. The apparatus exerts a steadily increasing force and reaction thresholds were determined as the pressure (g) required to elicit paw withdrawal. Each reaction threshold measure was repeated three times for both hind paws with intervals of approximately 2-3 min.

Experimental Design

Six (6) groups of 10 rats were employed.

| | |
| --- | --- |
| Group 1: | HBSS, intra-tibial, solution + 0.9% NaCl, intraplantar, solution |
| Group 2: | 30,000 MRMT-1 cells in HBSS, intra-tibial, solution + 0.9% NaCl, intraplantar, solution |
| Group 3: | 30,000 MRMT-1 cells in HBSS, intra-tibial, solution + BoNT/A (Dysport 5 U/kg) in 0.9% NaCl, intraplantar, solution |
| Group 4: | 30,000 MRMT-1 cells in HBSS, intra-tibial, solution + BoNT/A (Dysport 10 U/kg) in 0.9% NaCl, intraplantar, solution |
| Group 5: | 30,000 MRMT-1 cells in HBSS, intra-tibial, solution + BoNT/A (Dysport 20 U/kg) in 0.9% NaCl, intraplantar, solution |
| Group 6: | 30,000 MRMT-1 cells in HBSS, intra-tibial, solution + BoNT/A (Dysport 40 U/kg) in 0.9% NaCl, intraplantar, solution |
| Group 7: | 30,000 MRMT-1 cells in HBSS, intra-tibial, solution + morphine HCl, 3 mg/kg in 0.9% NaCl, s.c., solution |

Doses were expressed in terms of free active substance.

Vehicle and BoNT/A protease (Dysport) were administered by intraplantar route in the injured hind paw under a volume of 70 µl/kg with a 30 G needle.

Morphine was subcutaneously administered at 5 ml/kg.

Surgical Procedure

Bone cancer pain was induced by implantation of 30,000 MRMT-1 mammary carcinoma cells into the medullary cavity of the tibia in anaesthetized rats (Xylazine 10 mg/kg i.p., Ketamine 60 mg/kg i.p.) on D0.

A 1 cm rostro-caudal incision was made in the skin over the proximal half of the left tibia to expose the bone with minimal damage to the surrounding muscle or blood vessels. Using a 21 gauge needle, the bone was pierced and a thin catheter connected to a Hamilton syringue inserted, allowing it to reach the intramedullary canal of the tibia. 10 pi of the cell suspension (cancer group) or HBSS (sham group) was then gently injected. The injection site was closed using bone wax and surgical glue, thoroughly washed with 0.9% NaCl, and the wound closed with surgical suture.

Behaviour Testing

Eleven days after cancerous cells implantation (D11), paw withdrawal thresholds of the two hindpaws were measured (baseline) on all groups.

Rats from groups #1 to #6 received Vehicle or BoNT/A protease (Dysport®) by intraplantar injection into the left injured paw undergas anaesthesia (3.5% Isoflurane/3 L/min) with a 30 G needle.

Morphine was subcutaneously administered on D14 and on D21.

Rats were sacrificed at the end of the experiment by CO2 inhalation pending subsequent removal by a certified company.

Body Weight

Rats were weighed every day (except on Saturday and Sunday) from the surgery to D10 and each experimental day, before testing.

Data Presentation and Statistical Analysis

Results were expressed as (for each animal):
  The paw withdrawal threshold defined as the pressure in grams (g) applied onto each hind paw and calculated as the average of the three consecutive measures for each hind paw.

For each treatment group,
  The paw withdrawal threshold (mean±s.e.m.) calculated as the average of the animals
  The percentage of variation of the paw withdrawal threshold calculated from the mean value of the vehicle-treated group.

To determine a statistical effect of the test substance and the reference substance, data were analysed by a parametrical or non-parametrical test depending on the normal distribution of the results. The significance level was set at $p<0.05$.

Dissolving the lyophilisate

BoNT/A protease (Dysport®) was conditioned in a vial in lyophylisate form in a quantity of 500 U for the batch used.

The lyophilisate was dissolved with the appropriate volume of 0.9% NaCl in order to obtain a mother solution at 500 U/ml:
  filled a syringe with a 25G or 26G needle cross the septum in the middle and injected 1 ml avoiding bubbles.
  the syringe was removed quickly with the needle to avoid the vacuum suction.
  after the toxin was in solution it was possible to open the vial to add or not, precisely, with automatic pipette the volume to obtain a 500 U/ml solution.

This solution was employed as stock solution and stored at +4° C. during 24 hours.

Dilutions

The containers used for the dilution were glass and serial dilutions will be avoid.

At the end of each testing day, remaining solution of BoNT/A (Dysport®) was deactivated using 0.5% chlorine active solution of sodium hypochlorate. At the end of the experimental phase, remaining stock solution of BoNT/A (Dysport®) received 0.5% chlorine active solution of sodium hypochlorate.

In order to respect a volume around 20 pi/rat, the following solutions were prepared at the concentration presented below. Other solutions were prepared similarly:

TABLE 5

| Dose | Concentration of the solution | Volume of administration |
|---|---|---|
| 10 U/kg | 150 U/ml | 70 μl/kg |
| 20 U/kg | 300 U/ml | 70 μl/kg |
| 30 U/kg | 450 U/ml | 70 μl/kg |

Example 1

BoNT/A Protease (Dysport® at 10-40 U/kg) Dose-Curve Study

The effect of a single intraplantar administration of BoNT/A protease (Dysport®) was assessed in a rat model of MRMT-1 induced bone cancer pain—see FIG. 1. Acute intraplantar administration of BoNT/A protease (Dysport®) produced dose-dependent and time-dependent reversal of deficit in paw withdrawal threshold, thus reducing allodynia induced by bone cancer.

Example 2

Comparative Morphine Studies

Figure 2:
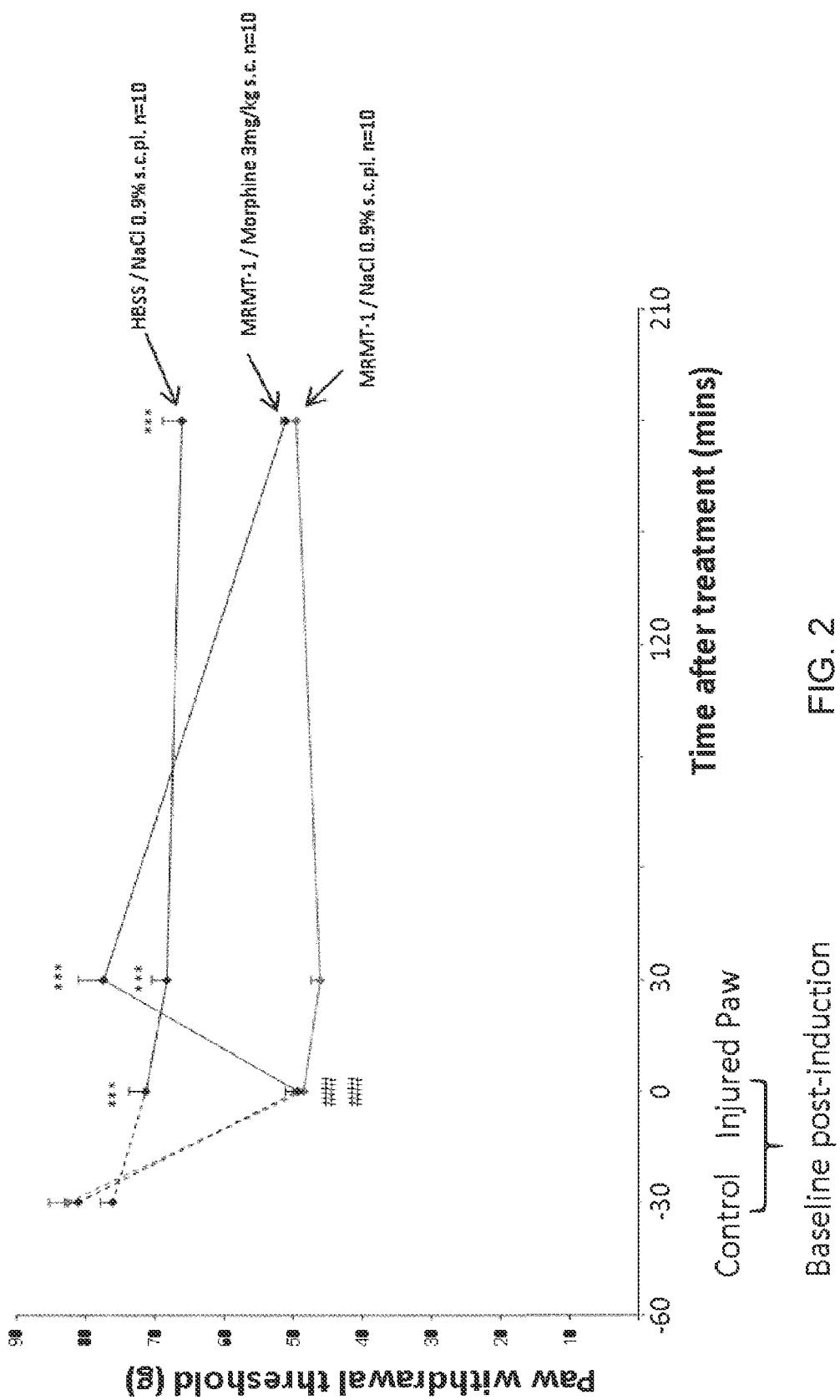
FIGS. 2 and 3 show comparative studies, showing the effect of a single administration of morphine, as assessed in the rat model of MRMT-1 induced bone cancer pain.
Figure 3:
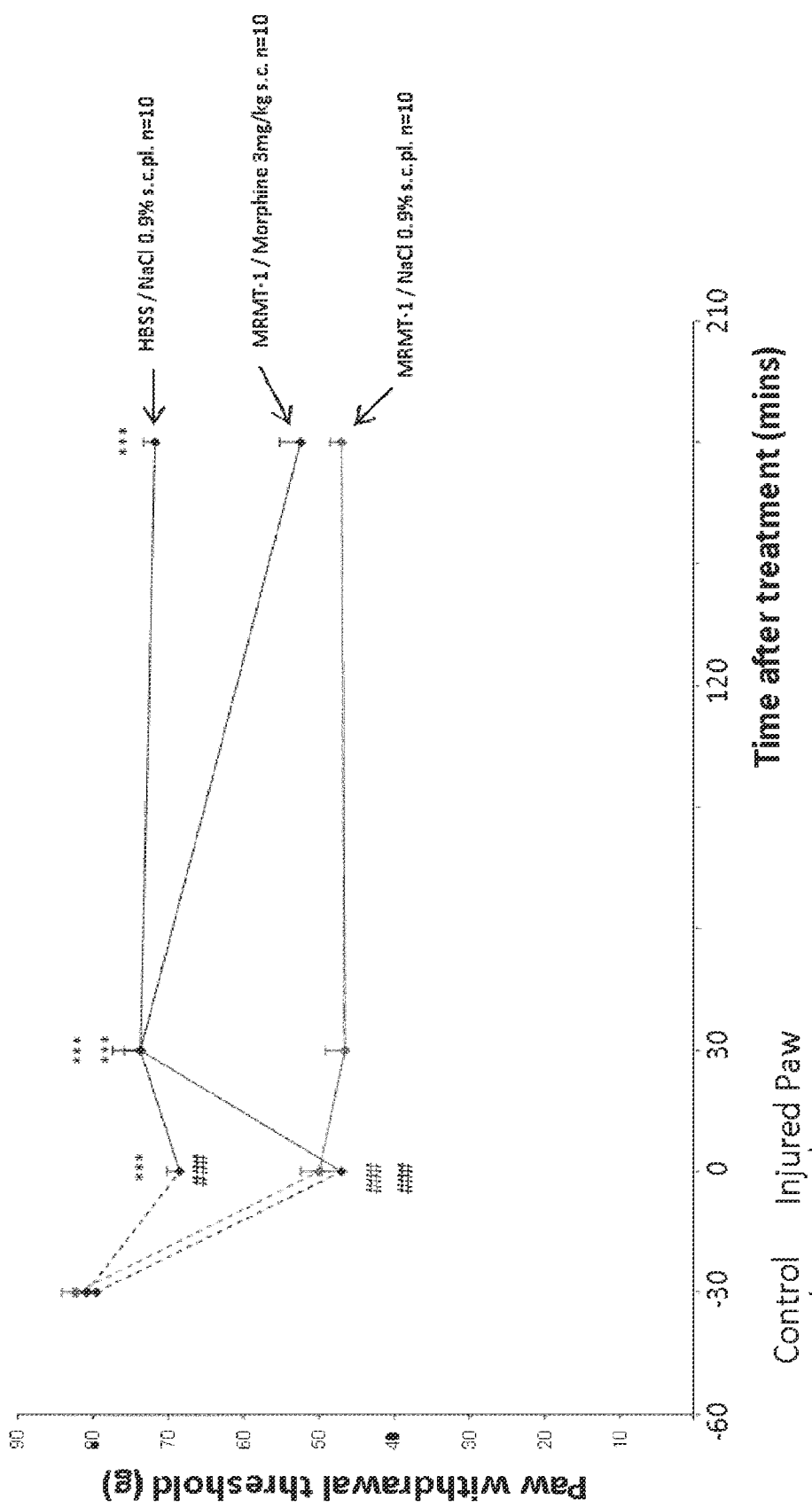

In comparative studies, the effect of a single administration of morphine was assessed in the same rat model of MRMT-1 induced bone cancer pain. Morphine was administered on $D_{14}$ (see FIG. 2) or $D_{21}$ (see FIG. 3) after cancerous cells implantation. Results demonstrate a reversal of deficit in paw withdrawal threshold, thus demonstrating a reduction in allodynia induced by bone cancer.

These results are complementary to the results obtained for a non-cytotoxic protease (BoNT/A) shown in Example 1, demonstrating that an analgesic molecule (e.g. an opiate, such as morphine) may be co-administered with a non-cytotoxic protease to provide a synergistic suppression of bone-induced allodynia.

Example 3

Comparative Rat Body Weight Studies

Corresponding rat body weights were monitored in studies comparative to Example 1, though employing slightly different BoNT/A protease (Dysport®) dosages. The effect of a single local administration of BoNT/A protease (Dysport®) was assessed in the same rat model of MRMT-1 induced bone cancer pain. Body weights (Table 6) were assessed after administration of BoNT/A protease corresponding to $D_{11}$ to D21 after cancerous cells implantation.

TABLE 6

| | Body Weight (g) | | | | |
|---|---|---|---|---|---|
| Groups | D11 | D12 | D14 | D18/D19 | D21 |
| HBSS/Vehicle | 297 | 302 | 320 | 358 | 370 |
| MRMT-1/Vehicle | 322 | 325 | 345 | 387 | 403 |
| MRMT-1/BONT/A (Dysport 10 U/kg) | 330 | 334 | 353 | 385 | 402 |
| MRMT-1/BONT/A (Dysport 20 U/kg) | 313 | 318 | 334 | 361 | 367 |
| MRMT-1/BONT/A (Dysport 30 U/kg) | 324 | 329 | 343 | 364 | 376 |

Results expressed as mean±s.e.m.

The invention claimed is:

1. A method for suppressing bone cancer-induced allodynia in a patient diagnosed with bone cancer, the method comprising administering a therapeutically effective amount of a non-cytotoxic protease to the patient.

2. The method of claim 1, wherein the bone cancer is a metastatic bone cancer.

3. The method of claim 1, wherein the patient has an additional cancer other than bone cancer.

4. The method of claim 1, further comprising administering an analgesic molecule.

5. The method of claim 4, wherein the analgesic molecule is administered in an amount that does not suppress bone cancer-induced allodynia in the patient when administered in the absence of the non-cytotoxic protease.

6. The method of claim 4, wherein the allodynia is tactile allodynia and/or dynamic allodynia.

7. The method of claim 4, wherein administration of the non-cytotoxic protease is effected at a structurally damaged bone, a periosteal irritation, a nerve entrapment, and/or other compromised area.

8. The method of claim 7, wherein administration is: proximal to a local concentration of bone cancer cells, direct into bone cancer cells, or into connective tissue.

9. The method of claim 1, wherein the non-cytotoxic protease is a clostridial neurotoxin, an antarease protease, or an IgA protease.

10. The method of claim 9, wherein the non-cytotoxic protease is a botulinum neurotoxin.

11. The method of claim 1, wherein the non-cytotoxic protease is administered at a dose of from 1 to 100 U/kg patient.

12. The method of claim 3, wherein the additional cancer is a lung cancer, a breast cancer, or an ovarian cancer.

13. The method of claim 4, wherein the analgesic molecule is an opiate.

14. The method of claim 12, wherein the opiate is morphine.

15. The method of claim 4, wherein the analgesic molecule is administered simultaneously with the non-cytotoxic protease.

16. The method of claim 4, wherein the analgesic molecule is administered at a different time from the administration of the non-cytotoxic protease.

17. The method of claim 10, wherein the botulinum neurotoxin is BoNT/A.

18. The method of claim 11, wherein the non-cytotoxic protease is administered at a dose of from 10 to 50 U/kg patient.

* * * * *